(12) United States Patent
O'Keefe, Jr. et al.

(10) Patent No.: US 10,078,952 B2
(45) Date of Patent: Sep. 18, 2018

(54) BED CHECK DEVICE AND METHOD OF USE

(71) Applicants: Patrick John O'Keefe, Jr., Wellington, OH (US); David Patrick O'Keefe, New London, OH (US)

(72) Inventors: Patrick John O'Keefe, Jr., Wellington, OH (US); David Patrick O'Keefe, New London, OH (US)

( * ) Notice: Subject to any disclaimer, the term of this patent is extended or adjusted under 35 U.S.C. 154(b) by 0 days.

(21) Appl. No.: 15/341,796

(22) Filed: Nov. 2, 2016

(65) Prior Publication Data

US 2017/0124840 A1 May 4, 2017

Related U.S. Application Data

(60) Provisional application No. 62/249,453, filed on Nov. 2, 2015.

(51) Int. Cl.
| | |
|---|---|
| *G08B 23/00* | (2006.01) |
| *G08B 21/04* | (2006.01) |
| *G01L 1/20* | (2006.01) |
| *A47C 31/00* | (2006.01) |
| *A47D 15/00* | (2006.01) |
| *G01G 19/52* | (2006.01) |
| *G01G 19/00* | (2006.01) |

(52) U.S. Cl.
CPC .......... *G08B 21/0461* (2013.01); *A47C 31/00* (2013.01); *A47D 15/00* (2013.01); *G01L 1/20* (2013.01)

(58) Field of Classification Search
CPC .... G08B 21/0461; A47C 31/00; A47D 15/00; G01L 1/20

USPC ........................................................ 340/573.4
See application file for complete search history.

(56) References Cited

U.S. PATENT DOCUMENTS

| | | | | |
|---|---|---|---|---|
| 3,722,611 | A * | 3/1973 | Tirkkonen | ................ A61G 7/00 177/144 |
| 4,263,586 | A * | 4/1981 | Nicholas | ................ A61B 5/1115 200/85 R |
| 4,657,026 | A * | 4/1987 | Tagg | .................... A61B 5/1102 600/534 |
| 5,640,145 | A | 6/1997 | Newham | |
| 6,239,706 | B1 * | 5/2001 | Yoshiike | ................ G08B 21/22 340/573.4 |
| 7,381,910 | B1 * | 6/2008 | Wilkerson | ........... G01G 19/445 177/144 |
| 8,783,114 | B2 | 6/2014 | Anderson et al. | |
| 9,013,313 | B2 * | 4/2015 | Paine | .................. G08B 21/0461 340/286.07 |
| 2002/0070867 | A1 * | 6/2002 | Conway | ............. G08B 21/0446 340/573.1 |
| 2004/0124017 | A1 * | 7/2004 | Jones | .................... G01G 19/445 177/144 |

(Continued)

*Primary Examiner* — Jack K Wang
(74) *Attorney, Agent, or Firm* — Emerson, Thomson & Bennett, LLC; Roger D. Emerson

(57) ABSTRACT

A bed check device having a force sensing resistor; a resistor divider; a microprocessor; an analog to digital converter; a power supply; a wireless transmitter; and an antenna wherein the force sensing resistor is in mechanical contact with a bed, such that a change in force to the bed corresponds to a change in its resistance and voltage, which is analyzed and acted upon by the resistor divider, microprocessor, analog to digital converter, power supply, wireless transmitter, and antenna.

20 Claims, 6 Drawing Sheets

(56) References Cited

U.S. PATENT DOCUMENTS

| | | | |
|---|---|---|---|
| 2006/0175097 A1* | 8/2006 | Pirzada | G01G 19/445 177/145 |
| 2009/0051549 A1 | 2/2009 | Tochigi et al. | |
| 2009/0260158 A1* | 10/2009 | Kazuno | A61B 5/1115 5/600 |
| 2011/0156915 A1 | 6/2011 | Brauers et al. | |
| 2012/0154155 A1 | 6/2012 | Brasch | |
| 2014/0076644 A1* | 3/2014 | Derenne | A61G 7/012 180/19.2 |
| 2014/0352060 A1 | 12/2014 | Hirose | |

* cited by examiner

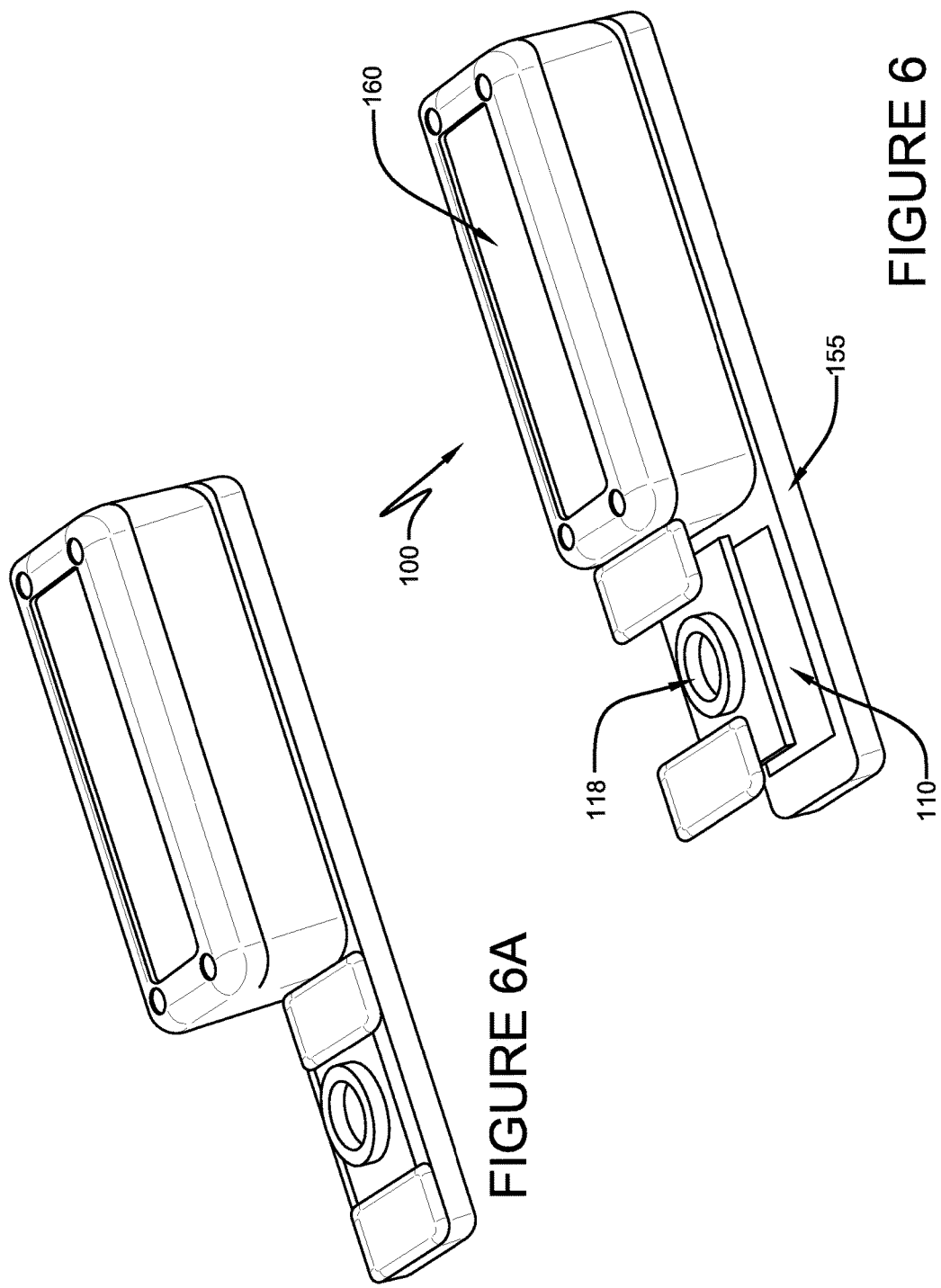

BED CHECK DEVICE AND METHOD OF USE

TECHNICAL FIELD

The present invention relates to apparatuses and methods for monitoring the status of a person in bed. More particularly, the present invention is directed at a system that is capable of detecting the status of a person in a bed, and reporting the status to an intended recipient, such as a caretaker.

BACKGROUND

Putting a child to bed is an important part of the day for a parent as well as for the child. It is important for the child to get a good night of sleep, and it is important for the parent to know that the child is safely in bed. One of the issues with putting a child in bed is making sure that they will stay in bed and sleep, and not try to get up and move around the house. This is an age-old problem with children who are either not tired, or want to stay awake for some other reason. Many potential issues can arise if a child is out of bed without knowledge of the parent or caretaker.

Often it is preferable to monitor other persons' sleep habits, such as the elderly, the ill, or persons affected by sleepwalking or other sleep disorders as many of the same issues presented by children at bed time can affect other persons as well.

There are solutions available in the market for detecting when people of all ages are out of bed, but these can be prone to false alarms, e.g. if a child stirs, it may send a warning to a parent that the child is out of bed. Many of the present solutions are systems created specifically for elderly patients in hospital or assisted-living type settings. These types of solutions can render false readings because they may not be properly calibrated for the more aggressive movements of a child. Additionally, many of the solutions are integrated into a hospital-type bed, which can be cost prohibitive.

A Force Sensing Resistor (FSR) can be less expensive than other force measuring devices, such as a force cell or piezoelectric devices. However, an FSR cannot provide an accurate measure of force, such as a precision scale. These devices are typically used in applications such as a button, where force is applied momentarily and then fully released, the resistance change can be very large and the two states (press/release) can be easily determined. When used with a constant load, there are issues that can arise that need correction if a robust indication in change of force is to be enjoyed. Additionally, the FSR can exhibit other disadvantages, such that it can have poor repeatability even with a momentary addition/removal of the same weight; it can vary its value with temperature; it can drift significantly—usually the resistance can drift down under constant load over time, especially if there is a constant load on the FSR—such as the weight of an empty bed—or constant load of bed plus an occupant. This drift can be accentuated when the sensor is placed on a carpet, especially at first as the sensor sinks into the carpet.

Thus, a key issue to be overcome when monitoring children is the relative weight of the child to the bed that needs to be differentiated by the bed check device circuitry when there is a small change in resistance in the FSR, unlike a button press as given in an earlier example. Comparatively, it is also much easier to see a large change in weight of an adult relative to the existing weight of a bed. Typical values for a bed sensors for children are as follows: The bed can weigh ~12-26 pounds; Average toddler boys can weigh 17.5 to 38 pounds; Average toddler girls can weigh 19 to 38 pounds. The relatively small difference between the weight of the bed leg and the weight of a child can be challenging to discern, especially combined with the drift and other issues cited above with FSR technology. To overcome this, the FSR needs to be continuously calibrated.

Another potential issue is the removal of noise and other errant readings. Since the detection circuitry needs to be able to detect a smaller range of weight differences, as with children, it need to thus be more sensitive. However this sensitivity can create issues such as false readings caused by, for example, the floor shaking as people are walking or running in the house, a clothes washer or dryer shaking the floor under the sensor, or a wiggly child in the bed, crawling across the bed, or jumping up and down in the bed, causing false alarms.

Accordingly, there is a need for a device that can enjoy the benefits of using an FSR to monitor a child's presence in the bed, while overcoming its disadvantages. What is needed is a cost effective, reliable solution that can accurately alert a caretaker to let them know if and when a child or other person has left their bed.

SUMMARY

Provided is a bed check device having a force sensing resistor; a resistor divider; a microprocessor; an analog to digital converter; a power supply; a wireless transmitter; and an antenna wherein the force sensing resistor is in mechanical contact with a bed, such that a change in force to the bed corresponds to a change in its resistance and voltage, which is analyzed and acted upon by the resistor divider, microprocessor, analog to digital converter, power supply, wireless transmitter, and antenna.

DESCRIPTION OF THE DRAWINGS

FIG. 6 is an exploded perspective view of the present invention and Force Sensing Resistor that can be used in the present invention.

FIG. 6A is a non-exploded perspective view of the present invention and Force Sensing Resistor that can be used in the present invention.

DETAILED DESCRIPTION

Given the extra sensitivities involved with a person having a low body mass and weight, such as a child, the description is directed at the application of the present invention for the monitoring of a child. While this is the disclosed use, the disclosed device and method can easily be adapted by a person of skill in the art for use with persons of all ages and sizes, and the invention described herein should be understood to include such adaptations within the scope of the disclosure.

Figure 1:
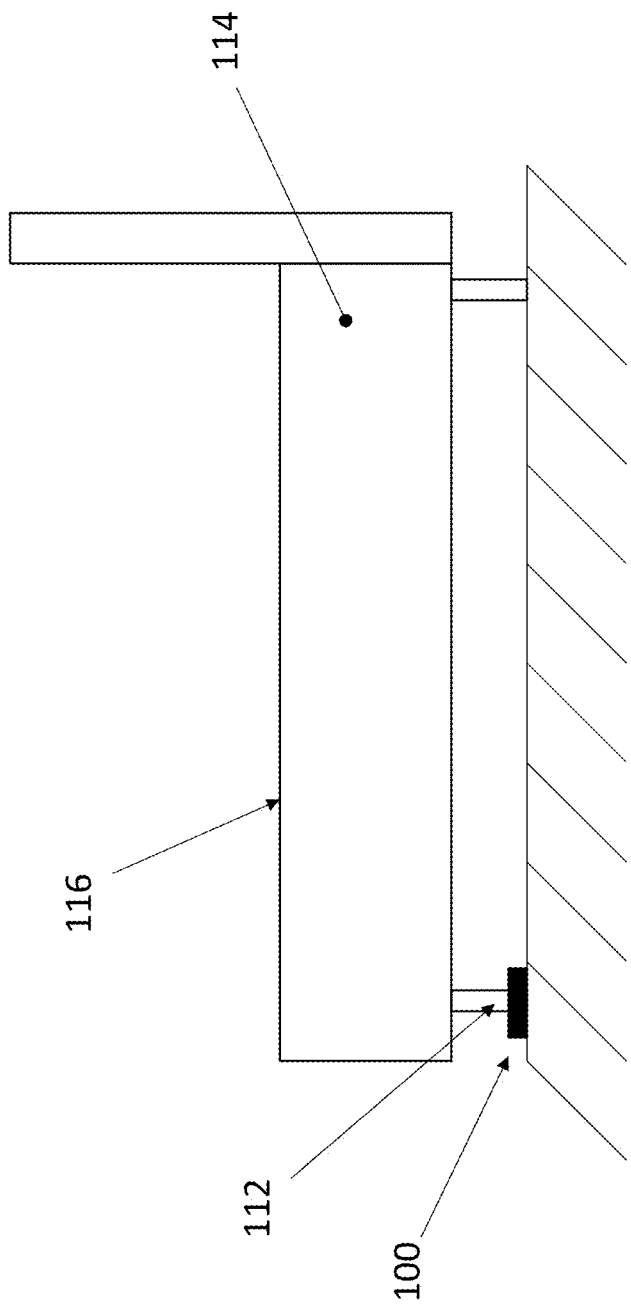
FIG. 1 is a diagram showing an embodiment of a Force Sensing Resistor that can be used in the present invention.

With reference to FIG. 1, according to one embodiment, a bed check device 100 can be attached to the leg 112 of a bed 114. The bed check device 100 can be placed under the leg of the bed 114, as shown; however it can also be mounted directly to the bed 114, or onto the side of the leg 112, or in any appropriate manner. The bed 114 can also be a crib, bassinette, or the like. A child can get into bed, either by being placed upon the bed or by moving onto the surface 116 of the bed.

Figure 2:
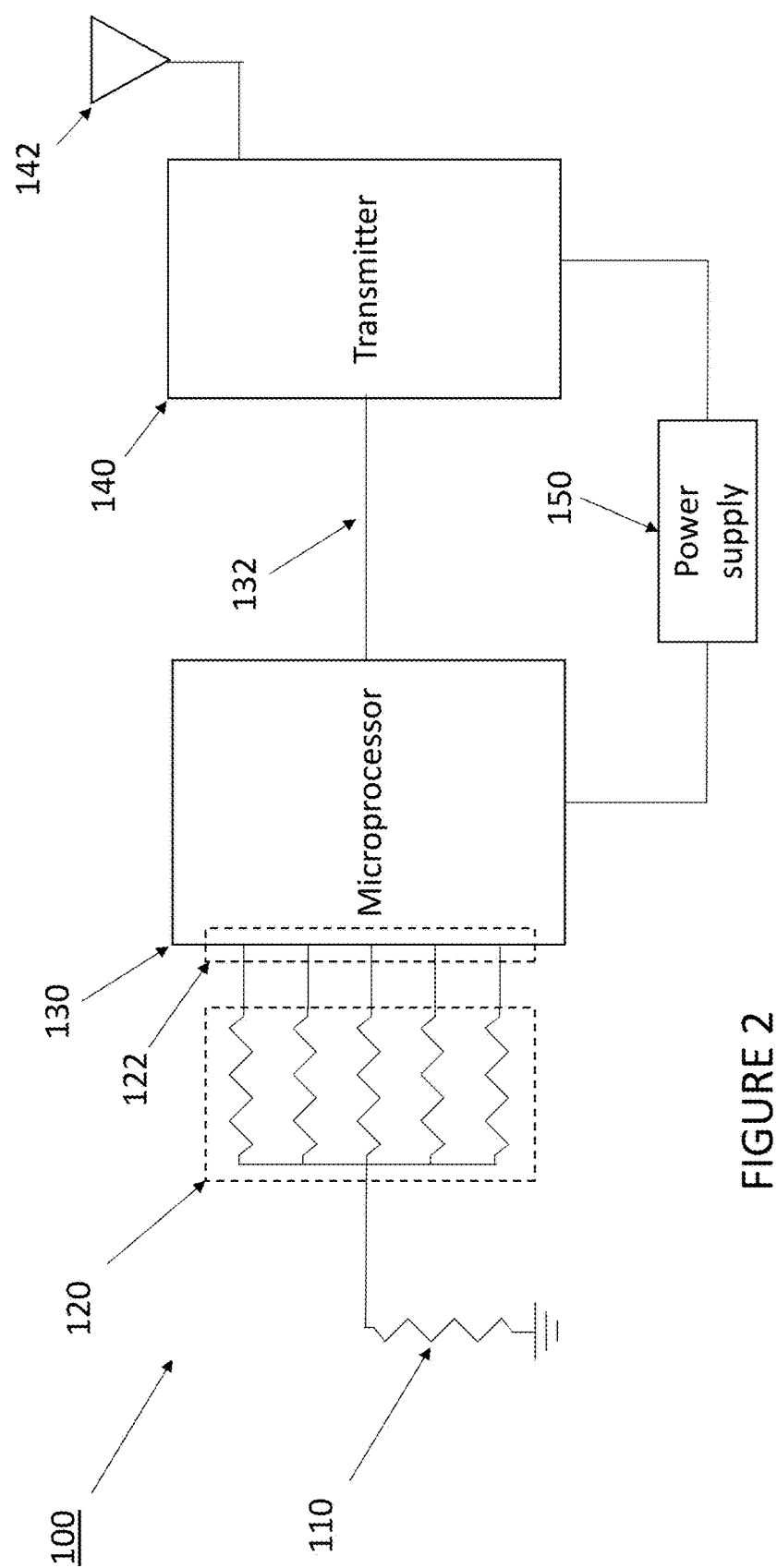
FIG. 2 is a schematic diagram of a control circuit for the present invention.

With reference to FIG. 2, according to this embodiment, the bed check device 100 can have a force sensing resistor (FSR) 110 that can be connected on one side to ground, and on the other side to a voltage divider circuit 120 that can be likewise connected to a microprocessor 130 via a set of corresponding inputs 122. Thus, a voltage on the inputs 122 will correspond to an applied force to the FSR 110. The microprocessor 130 can have an integrated analog to digital converter (A/D) and can be connected via a data link 132 to a transmitter 140 that can be connected to an antenna 142. A power supply 150 can be connected to the microprocessor 130 and transmitter 140. The power supply can be a standard or rechargeable battery, or AC-DC power adapter, or the like.

Figure 3:
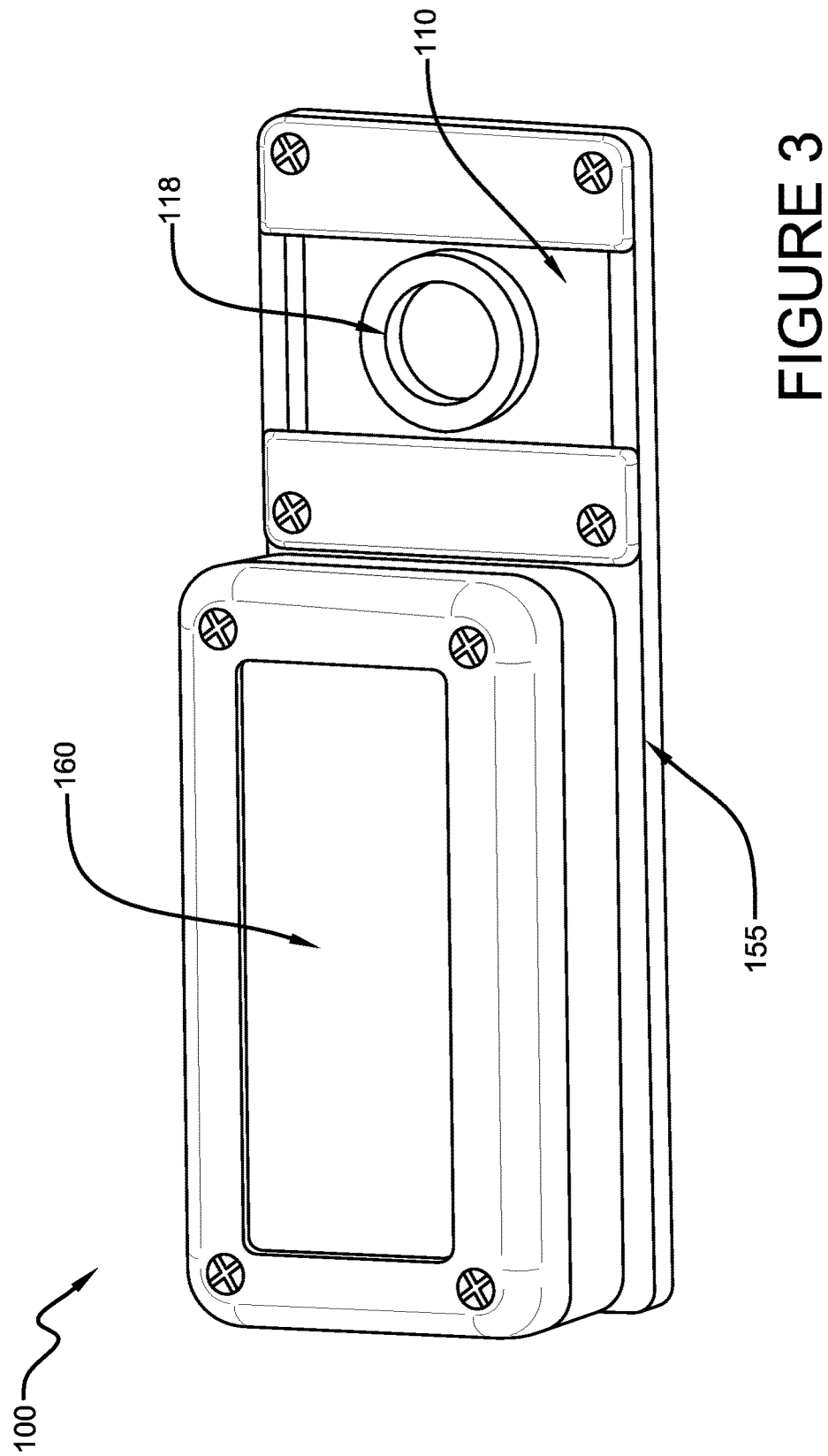
FIG. 3 is a perspective drawing of the present invention and Force Sensing Resistor that can be used in the present invention.

With reference to FIGS. 1 and 3, according to this embodiment, the bed check device 100 can be assembled into a housing 160 which can be mounted on a base 155 as shown. All of the electronic components from FIG. 2 can be contained in the housing 160, except that the FSR 110 can extend from the housing in order to be placed under a bed leg 112. The FSR 110 is sandwiched between the base 155 and a plate which can have an indent 118 so that the bed leg 112 can be placed in the center of the FSR 110 and can have limited movement from that location. According to another embodiment, the FSR 110 can also be placed within an additional layer of thin material, such as plastic or polymer, on each side as recommended by the manufacturer to help distribute the load more evenly across the surface of the FSR 110. The bed check device base 155, as shown in FIG. 3, can have rounded edges and smooth surfaces, such that it can slide on the floor if children bump the bed during play.

With continued reference to FIGS. 1 and 2, the bed check device can automatically calibrate itself, while in an "out of bed mode", to compensate for the drift in resistance value of the FSR 110. In one embodiment, it can do this by sequentially switching each of the resistors, one at a time, in divider network 120 into the circuit with FSR 110. The microprocessor can switch each resistor in divider 120 independently into the circuit with FSR 110 until it measures a voltage that is closest to the middle of the typical voltage of 3.3 volts. This measurement is accomplished by the integrated A/D in the microprocessor 130. The measured voltage will change depending upon the selected resistor from the divider 120. The values of the resistors in divider 120 can range from the hundreds of ohms to tens of thousands of ohms and can be chosen dependent upon the resistance value of the FSR 110. When the microprocessor 130 switches in the various resistors during calibration, the non-selected resistors can be placed into a high-impedance state, such that they cannot affect the A/D voltage on the selected resistor. The microprocessor 130 can be programmed to perform a calibration every time an "out of bed" mode is established, which can continuously compensate for the inherent long term drift of the FSR 110. In certain embodiments, changing the resistor or effective resistance for the above automatic calibration may be done by a set or resistors in parallel or an adjustable potentiometer. With a set or resistors in parallel one or more switches operatively engaged with the device may be used to switch each resistor and take a measurement with each resistor in order to obtain the above referenced a voltage measurement that is closest to the middle of the typical voltage of 3.3 volts. Alternatively, an adjustable potentiometer, such as, without limitation, a digitally adjustable potentiometer or a rheostat, may be set to a variety of resistances with measurements taken at each resistance to determine the resistance which produces the middle of the typical voltage of 3.3 volts. It should be understood that, as used herein, "resistor" may refer to an adjustable potentiometer With continued reference to FIGS. 1 and 2, according to this embodiment, a child can impinge on the bed surface 116, and this can cause a change in force on the bed leg 112, applying force to the FSR 110. When a force is applied to the FSR 110, its resistance can decrease rapidly over a large range. In one embodiment, the resistance may decrease from tens of thousands of ohms to hundreds of ohms. This change in resistance can cause a change in voltage on the selected resistor, and microprocessor 130 can measure this voltage on the selected resistor that was determined during the calibration stage using the integrated A/D in the microprocessor 130. After calibration, and during normal operation, the microcontroller 130 can sample the voltage on the selected resistor every few milliseconds, in one embodiment. The voltage value of the force can be memorized or recorded at each sample and the current sample can be subtracted from the previous sample. An absolute value of the difference between subsequent samples can be calculated.

Figure 4:
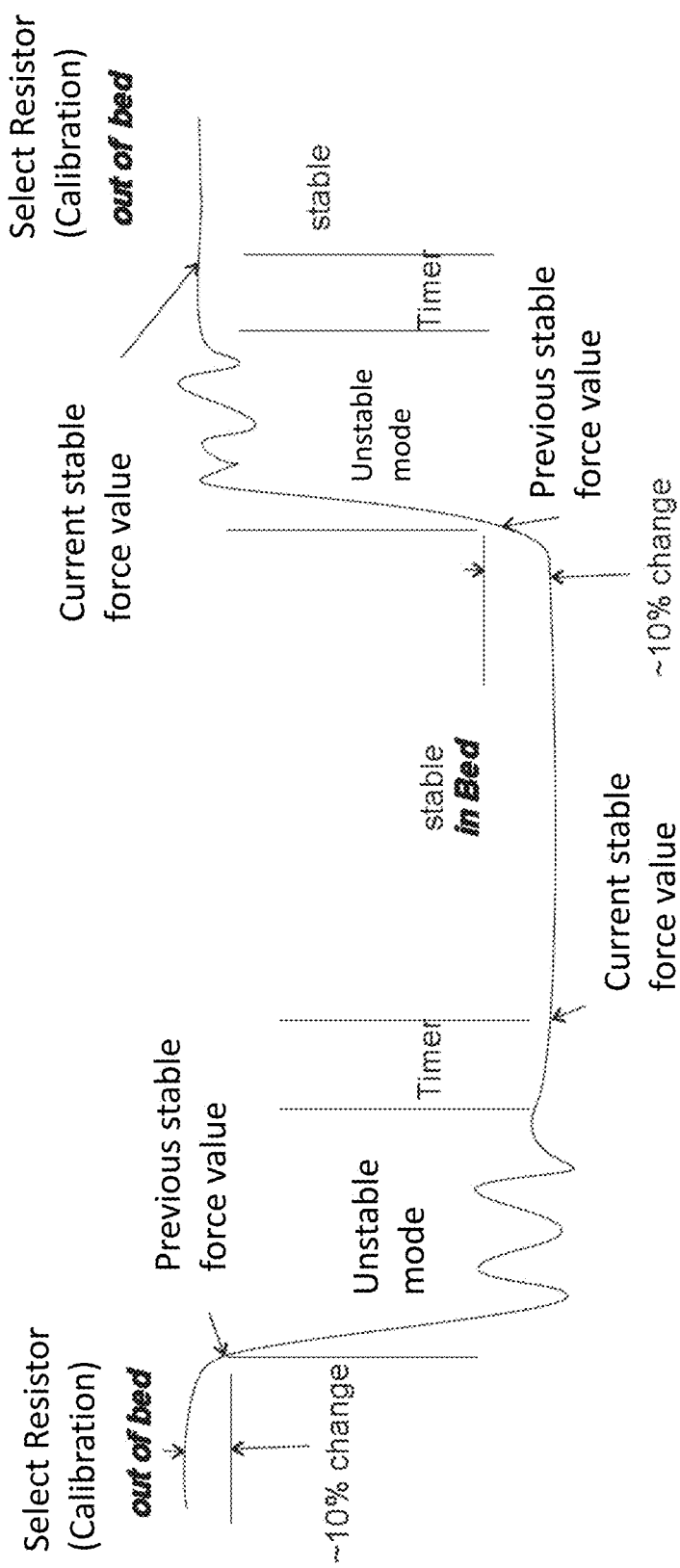
FIG. 4 is a mode-time diagram that shows the various possible modes as a function of time, as an embodiment used by the present invention.

With reference to FIG. 4, starting from the left, a typical waveform of the voltages that appear to the A/D converter is shown. There can be four modes of operation: "in bed", "out of bed", "stable", and "unstable". In addition, there can be a "previous stable force value" that represents the last known stable force value, and the "current stable force value" which represents the most newly acquired stable force value. These values will be discussed below. The voltage value for "out of bed" mode will be higher than the "in bed" since the FSR 110 voltage decreases with applied force. This example starts with an "out of bed" mode with calibration and resistor selection as previously described. If a child now enters the bed, the voltage on the FSR 110 can vary. This variation can also potentially be caused by the child wiggling during sleep, or intermittent disturbances from external, unintended sources such as people walking on floors, closing doors, laundry machines, children playing, and the like. The calculation of the absolute value of the difference between subsequent samples may be compared to a first threshold value. The first threshold value may be the voltage value just prior to the initiation of instability. As shown in FIG. 4, when the calculation of the absolute value of the difference between subsequent samples exceeds the first threshold, with an exemplary value of ~10% change, the microprocessor 130 can enter an "unstable mode". The value of the force just prior to entering the unstable mode may also be memorized or recorded as a "Previous stable force value". As long as the absolute value remains above the threshold, the unit can continue in the "unstable mode". After being in the unstable mode, and the absolute value decreases below a threshold, a programmable timer for several seconds long can be started in the microprocessor 130 to make sure that the instability has passed. A "Current stable force value" can then be memorized or recorded. If the unit is previously in an "out of bed" mode, and if the current stable value is less than the previous stable value by a mode threshold amount, the mode is changed to "in bed". If the unit is previously in an "in bed" mode, and if the current stable value is greater than the previous stable value by a predetermined "mode threshold amount", the mode is change to "out of bed". If the unit is in either mode, and the previous/current stable readings are not greater than the "mode threshold amount" the unit does not change modes.

In certain embodiments when the calculation of the absolute value of the difference between subsequent samples exceeds the first threshold the device may monitor the signal for peaks and valleys. Such monitoring of the signal for peaks and valleys may provide data usable to more accurately determine whether the condition of the signal is stable or unstable.

With continued reference to FIG. 4, while the microprocessor 130 is in "in bed" mode, if a child can then exit the bed, there can be a period of "unstable mode" as the subsequent samples exceed a calculated threshold value, and when the threshold is no longer exceeded, a timer is started in the microprocessor 130, and a "Current stable force" value can then be memorized. If this "current stable value" can be greater than the "Previous stable force value" by a second threshold, the "mode threshold amount", the mode can change to "out of bed".

Figure 5:
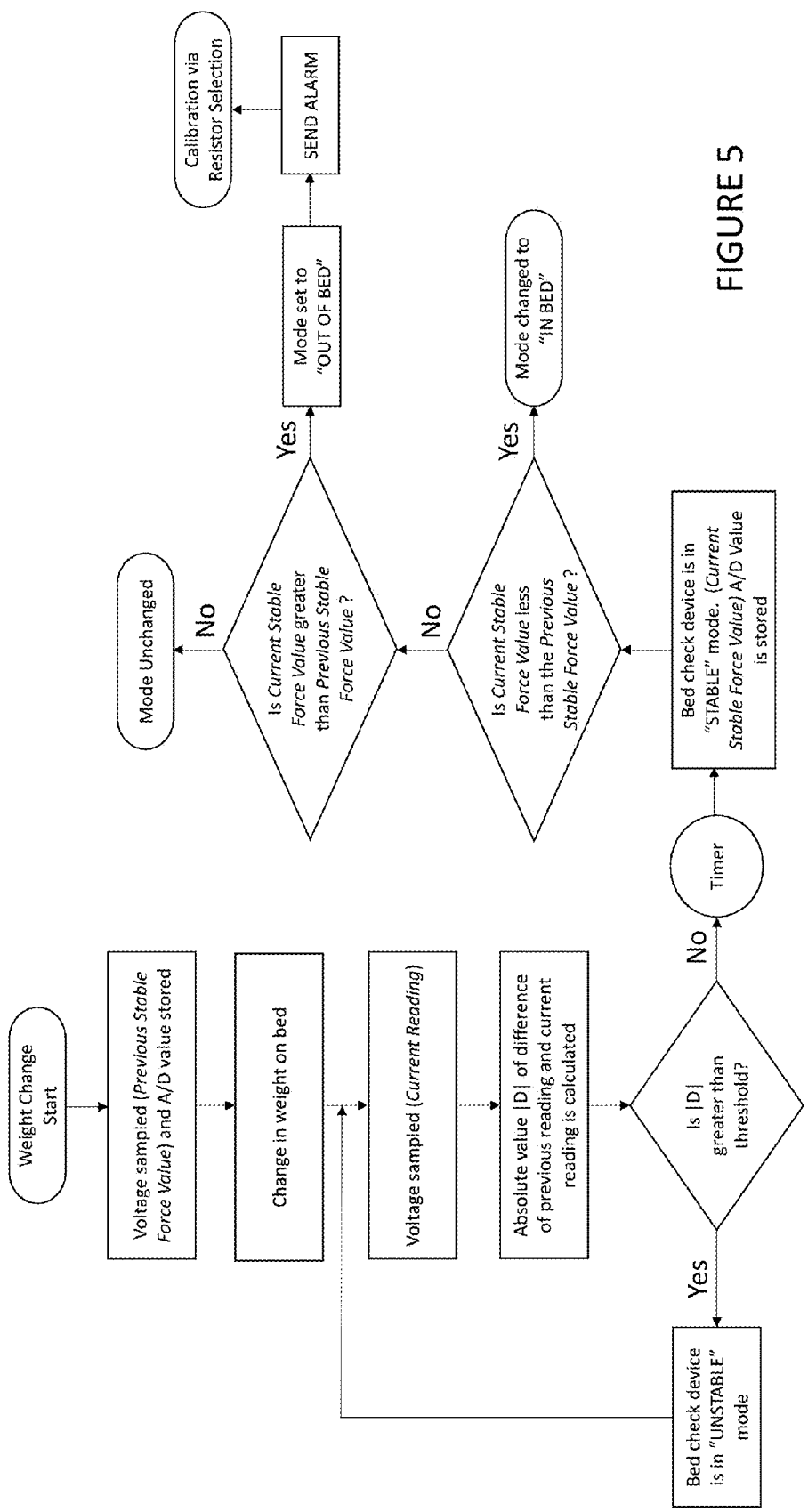
FIG. 5 is a flowchart of an embodiment of the method of control for the present invention.

With reference to FIG. 5, a flowchart for the mode changing process is shown. The oval symbols indicate the beginning and possible outcomes, with rectangular boxes indicating general operations. Diamond shape boxes indicate a comparison operation. The process begins with a stored "Previous stable force value". When a weight change, a change it the load state, is detected by the FSR 110, the absolute difference of the new voltage and the previously acquired voltage can be calculated. If this calculation can exceed a threshold, then the bed check device 100 can be in "unstable mode" and the voltage can be sampled again. This can continue until the threshold is not exceeded. Then a timer can be started to make sure that the instability has passed. The bed check device 100 can now be in "stable mode" and the "current stable force value" can be stored. This "current stable force value" can be compared to the "previous stable force value". If it is lower, by a predetermined threshold, the mode can be changed to "in bed". If it is higher, by a predetermined threshold, the mode can be changed to "out of bed". If the mode is changed to "out of bed", the bed check device 100 can then automatically calibrate itself using the resistor selection process as described earlier.

With continued reference to FIG. 2, when a mode change occurs, the microprocessor 130 can send an alert using the transmitter 140 and antenna 142. For example, this alert can be sent when the mode changes to "out of bed". In an embodiment, the alert can consist of sending a prepared text message such as "CHILD IS OUT OF BED" that can be transmitted to the internet via Wi-Fi, SMS, or the like. The message can be sent as an encoded, secure message. This message can also be stored, along with metadata such as time, date, etc. either in the bed check device 100 or to a remote computer server location, such as in "the cloud" or the like. The message and metadata can then be retrieved at a later time. The data that can be acquired over time for when the child enters and exits the bed can be useful for the caretakers of the child in determining sleep patterns. In alternative embodiments, the microprocessor can also transmit the message and, optionally, some or all of the other data referred to above to a security monitoring service via the internet or other secure network. Likewise, there can be an audible alarm that indicates the child is out of bed. Alternatively or additionally, the message and, optionally, some or all of the other data referred to above can be sent telephonically as an audio message to a telephone number. For the situation when a child is placed into bed, a text message can be sent which can provide a bed check device system check. This can provide confidence that all is well with the internet or other wireless data connection, and the sensor has not been dislodged from the leg of the bed, and that the batteries or power supply are functioning properly as the child is placed in bed. Additionally, since the bed check device 100 can have a connection to the internet, a user, such as a caretaker, can "ping" the device from a remote location to acquire the current mode, status, or other information.

In one embodiment the bed check device may be provide output through application software ("app") that is adapted to causes a computer, smartphone, and/or other mobile device to perform a task. In one such embodiment, a cloud set up may receive data from the device 100. The cloud may have an email address to which send a message chosen based on the received data. An app, without limitation, phone based or web site based, may permit a user to do some or all of the following: add phone numbers for alerts, add email addresses for alerts, indicate or receive indications of normal nap times and bed times to eliminate bed indications during play, make modifications to thresholds or other parameters related to sensitivity, etc., and receive indications of low battery.

As described above, the present disclosure has been described with preferred embodiments thereof and it is understood that many changes and modifications to the described embodiments can be carried out without departing from the scope and the spirit of the present disclosure that is intended to be limited only by the appended claims.

We claim:
1. A bed check device comprising:
 a. single force sensing resistor;
 b. a voltage divider, wherein the voltage divider comprises a top having a set of resistors in a divider network in circuit with the single force sensing resistor;
 c. a microprocessor, wherein the microprocessor is connected in circuit with the voltage divider via a set of corresponding outputs;
 d. an analog to digital converter integrated within the microprocessor, wherein the voltage on the analog to digital converter corresponds to an applied force on the single force sensing resistor as the microprocessor places voltage on the selected resistor at the top of the voltage divider;
 e. a power supply connected to the microprocessor and to a wireless transmitter, wherein the wireless transmitter is connected to the microprocessor via a data link and wherein an antenna is connected to the wireless transmitter;
 wherein the single force sensing resistor is connected on one side to ground and on the other side to the voltage divider circuit, further wherein the microprocessor switches between each resistor, one at a time, applying a voltage to the selected resistor within the voltage divider circuit until it measures a voltage on the analog to digital converter that is closest to a typical voltage, thereby allowing the bed check device to automatically center the measurement in the range of operation of the analog to digital converter while in an "out of bed" mode to compensate for drift in resistance values of the force sensing resistor,
 wherein the single force sensing resistor is in mechanical contact with one leg of a bed, such that a change in force to the bed corresponds to a change in its resistance and voltage, which is analyzed and acted upon by the voltage divider, microprocessor, analog to digital converter, power supply, wireless transmitter, and antenna.

2. The bed check device of claim 1, wherein the measured voltage will change depending upon the resistor selected from the voltage divider circuit and when the microprocessor switches between the various resistors during centering of the voltage in the range of operation of the analog to digital converter, the non-selected resistors are placed into a high-impedance state so that they cannot affect A/D voltage on the selected resistor.

3. The bed check device of claim 2, wherein the voltage of the force sensing resistor is sampled through said selected resistor by the said analog to digital converter between every one and one thousand milliseconds.

4. The bed check device of claim 3, wherein said device has at least four operating modes, namely: In-bed, Out-of-bed, Stable, and Unstable.

5. The bed check device of claim 4, wherein said microprocessor is programmed to determine each said mode based on received inputs from said force sensing resistor.

6. The bed check device of claim 5, wherein said microprocessor is programmed to determine said Unstable mode, and will not allow a transition from an In-bed mode to an Out-of-bed mode, or vice versa, until it has determined that said Unstable mode has transitioned to a Stable mode and the comparison of a previous stable force value and a current stable force value warrants the transition and wherein the microprocessor is programmed to center the measurement in the range of operation of the analog to digital converter every time an "out of bed" mode is established to continuously compensate for long term drift inherent within the force sensing resistor.

7. The bed check device of claim 6, wherein the microprocessor selectively places each and any of the resistors in the network in series with the force sensing resistor and provides a voltage to the selected resistor in order to achieve a voltage that is substantially in the middle of the range of said analog to digital converter.

8. The bed check device of claim 7, wherein the transmitter can send a message to an intended recipient via Wi-Fi, text or SMS message, telephonic message, or any other electronic media or wireless protocol.

9. The bed check device of claim 7, wherein
after centering the measurement in the range of operation of the analog to digital converter and during normal operation, the microcontroller samples the voltage on the selected resistor every few milliseconds;
wherein the voltage value of the force is recorded at each sample,
wherein the microprocessor subtracts the voltage value of the current sample from the voltage value of the previous sample and calculates and records the absolute value of this difference;
wherein the calculation of the absolute value of the difference between subsequent samples is compared to a first threshold value, wherein the first threshold value is the voltage value just prior to initiation of instability;
wherein when the calculation of the absolute value of the difference between subsequent samples exceeds the first threshold value, the microprocessor enters the unstable mode and the value of the force just prior to entering the unstable mode is recorded as a previous stable force value;
wherein when the calculation of the absolute value of the difference between subsequent samples decreases below the first threshold value for a programmed amount of time measured by the microprocessor, a new current stable force value is recorded by the microprocessor.

10. The bed check device of claim 9,
wherein if the bed check device is previously in an "out of bed" mode and if the current stable force value is less than the previous stable force value by a mode threshold amount, the mode is changed to "in bed";
wherein if the bed check device is previously in "in bed mode" and if the current stable value is greater than the previous stable value by a predetermined mode threshold amount, the mode is changed to "out of bed"; and
wherein if the bed check device is in either the "out of bed" mode or the "in bed mode" and the previous or current stable readings are not greater than the mode threshold amount, the unit does not change modes.

11. The bed check device of claim 8, wherein the message is encoded.

12. The bed check device of claim 11, wherein the all of the components are contained within a housing and mounted on a base, and wherein the force sensing resistor is mounted on a portion of the base that extends from a side of the housing.

13. The bed check device of claim 12, wherein the base has rounded edges configured to allow it to slide over a floor.

14. The bed check device of claim 13, wherein the force sensing resistor is disposed between a top layer comprising a plate and the base, wherein the plate has an indent which houses the force sensing resistor and which corresponds in size to the leg of an associated bed to allow the leg of the bed to be placed over the bed check device in the center of the force sensing resistor and to limit movement of the bed with respect to the bed check device.

15. A method of operating a bed check device comprising:
providing a bed, crib or bassinette;
providing a bed check device wherein the device comprises:
a. a single force sensing resistor;
b. a voltage divider, wherein the voltage divider comprises a top having a set of resistors in a divider network in circuit with the single force sensing resistor;
c. a microprocessor, wherein the microprocessor is connected in circuit with the voltage divider via a set of corresponding outputs;
d. an analog to digital converter integrated within the microprocessor, wherein the voltage on the analog to digital converter corresponds to an applied force on the single force sensing resistor as the microprocessor places a voltage on the selected resistor at the top of the voltage divider;
e. a power supply connected to the microprocessor and to a wireless transmitter, wherein the wireless transmitter is connected to the microprocessor via a data link and wherein an antenna is connected to the wireless transmitter;
wherein the single force sensing resistor is connected on one side to ground and on the other side to the voltage divider circuit, further wherein the microprocessor switches between each resistor, one at a time, applying a voltage to the selected resistor within the voltage divider circuit until it measures a voltage on the analog to digital converter that is closest to a typical voltage using the analog to digital converter integrated within the microprocessor, thereby allowing the bed check device to automatically center the measurement in the range of operation of the analog to digital converter while in an "out of bed" mode to compensate for drift in resistance values of the force sensing resistor, and wherein the single force sensing resistor is in mechanical contact with one leg of a bed, such that a change in force to the bed corresponds to a change in its resistance and voltage, which is analyzed and acted upon by the voltage divider, microprocessor, analog to digital converter, power supply, wireless transmitter, and antenna which allows for a message to be sent wirelessly to an intended recipient;

providing a subject to use the bed, crib or bassinette; and operating the bed check device to determine the occupancy of the bed, crib or bassinette.

16. The method of claim 15, wherein the intended recipient is a mobile phone, tablet, desktop computer, or laptop computer.

17. A method of centering the analog to digital measurement of claim 15 in a range of operation, wherein when the device is in an "out of bed" mode, the microprocessor performs the following steps:

a. selects a first resistor in the resistor divider, effectively putting it in series with the force sensing resistor and applies a voltage to the selected resistor;
b. measures the voltage with the analog to digital converter;
c. compares it to a substantially middle range value;
d. if the voltage is within a threshold to the middle range value, keeps the first resistor as the selected resistor;
e. if the voltage is outside of a threshold to the middle range value, it de-selects the first resistor and selects the second resistor; and
f. repeats the selection, measurement, and comparison steps until a resistor that can most effectively achieve a middle range value is selected.

18. The method of claim 17, wherein the centering the measurement in the range of operation of the analog to digital converter is performed each time the bed check device enters the "out of bed" mode.

19. A method of operating a bed check device comprising:

providing a bed check device comprising:
a single force sensing resistor;
a voltage divider, wherein the voltage divider comprises a top having a set of resistors in a divider network in circuit with the single force sensing resistor;
a microprocessor, wherein the microprocessor is connected in circuit with the voltage divider via a set of corresponding outputs;
an analog to digital converter integrated within the microprocessor, wherein the voltage on the analog to digital converter corresponds to an applied force on the single force sensing resistor as the microprocessor places voltage on the selected resistor at the top of the voltage divider;
a power supply connected to the microprocessor and to a wireless transmitter, wherein the wireless transmitter is connected to the microprocessor via a data link and wherein an antenna is connected to the wireless transmitter;
wherein the single force sensing resistor is connected on one side to ground and on the other side to the voltage divider circuit, further wherein the microprocessor switches between each resistor, one at a time, within the voltage divider circuit until it measures a voltage that is closest to a typical voltage using the analog to digital converter integrated within the microprocessor, thereby allowing the bed check device to automatically center the measurement in the range of operation of the analog to digital converter while in an "out of bed" mode to compensate for drift in resistance values of the force sensing resistor,
wherein the single force sensing resistor is in mechanical contact with one leg of a bed, such that a change in force to the bed corresponds to a change in its resistance and voltage, which is analyzed and acted upon by the voltage divider, microprocessor, analog to digital converter, power supply, wireless transmitter, and antenna which allows for a message to be sent wirelessly to an intended recipient;

mechanically engaging the bed check device to one leg of a bed to produce a signal in the device representative of a load state of the bed;

performing an analysis of the signal where the analysis includes the steps of obtaining a first measurement of the voltage of the signal at a first time during a first period of substantial stability in the signal, conducting a first process wherein the first process has the steps of obtaining a subsequent measurement of the voltage of the signal at a time subsequent to the first time, and calculating a first quantity where the first quantity is the absolute value of the difference between the first measurement and the subsequent measurement comparing the first quantity to a predetermined threshold value, if the first quantity is greater than the predetermined threshold value, setting or maintaining a variable that represents the state of the device as unstable, and conducting the first process again, or if the first quantity is not greater than the predetermined threshold value, conducting a second process wherein the first process has the steps of setting or maintaining a variable that represents the state of the device as stable, and comparing the first measurement with the subsequent measurement if the subsequent measurement is less than the first measurement setting or maintaining a variable that represents the state of the device as "in bed", or if the subsequent measurement is greater than the first measurement setting or maintaining a variable that represents the state of the device as "out of bed".

20. The method of operating the bed check device of claim 19, wherein the second process further comprises the step of sending an alarm upon determining that the subsequent measurement is greater than the first measurement.

* * * * *